United States Patent [19]

Carman et al.

[11] Patent Number: 5,487,834
[45] Date of Patent: Jan. 30, 1996

[54] METHODS FOR MICROBIAL FILTRATION OF FLUIDS

[75] Inventors: Margaret L. Carman, San Ramon; Kenneth J. Jackson, San Leandro; Richard B. Knapp, Danville; John P. Knezovich, Stockton; Nilesh N. Shah; Robert T. Taylor, both of Livermore, all of Calif.

[73] Assignee: The Regents of the University of California, Oakland, Calif.

[21] Appl. No.: 15,237

[22] Filed: Feb. 9, 1993

[51] Int. Cl.⁶ .................................................. C02F 3/34
[52] U.S. Cl. ......................... 210/606; 210/611; 210/747; 210/910; 210/911; 435/262
[58] Field of Search ............................... 210/610, 611, 210/615–617, 747, 910, 911, 606; 435/262, 264

[56] References Cited

U.S. PATENT DOCUMENTS

| | | | |
|---|---|---|---|
| 2,142,196 | 1/1939 | Langdon | 210/7 |
| 3,979,283 | 9/1986 | Prudom | 210/11 |
| 4,664,805 | 5/1987 | Focht | 210/611 |
| 4,725,357 | 2/1988 | Downing et al. | 210/611 |
| 5,037,551 | 8/1991 | Barkley et al. | 210/610 |
| 5,196,339 | 3/1993 | Hanson et al. | 435/262 |
| 5,246,584 | 9/1993 | Donaldson et al. | 210/603 |

FOREIGN PATENT DOCUMENTS

WO89/09827  10/1989  WIPO.
WO90/01465  2/1990  WIPO.

*Primary Examiner*—Thomas S. Wyse
*Attorney, Agent, or Firm*—Henry P. Sartorio

[57] ABSTRACT

Novel methods for purifying contaminated subsurface groundwater are disclosed. The method is involves contacting the contaminated subsurface groundwater with methanotrophic or heterotrophic microorganisms which produce contaminant-degrading enzymes. The microorganisms are derived from surface cultures and are injected into the ground so as to act as a biofilter. The contaminants which may be treated include organic or metallic materials and radionuclides.

43 Claims, 4 Drawing Sheets

METHODS FOR MICROBIAL FILTRATION OF FLUIDS

REFERENCE TO GOVERNMENT CONTRACT

The United States Government has rights in this invention pursuant to Contract No. W-7405-ENG-48 between the U.S. Department of Energy and the University of California, for the operation of Lawrence Livermore National Laboratory.

TECHNICAL FIELD

This invention relates generally to the purification of fluids, and more particularly relates to a novel method and apparatus for purifying fluids using microorganisms which produce contaminant-degrading enzymes. The invention is particularly useful in conjunction with the decontamination of flowing groundwater.

BACKGROUND

Contamination of water with hazardous wastes such as toxic organic chemicals, metals or radionuclides is a problem of ever-increasing urgency. In particular, groundwater aquifers at many industrial and defense-related sites are contaminated with one- and two-carbon, volatile halogenated aliphatic hydrocarbons such as trichloroethylene ("TCE"), many of which are suspected carcinogens. (See, e.g., J. J. Westrick et al., *J. Am. Water Work Assoc.* 5:52 (1984) and P. F. Imfante and T. A. Tsongas, *Environ. Sci. Res.* 25:301 (1982)). Due to the natural flow of groundwater and dispersive transport processes, aquifer contamination at such sites has usually resulted in large, dilute migrating plumes that can extend tens of meters in depth. The contaminants are present in the aqueous phase and they are sorbed on the mineral phases that constitute a heterogeneous soil or rock. These physical characteristics of aquifer contamination make groundwater remediation to the concentrations mandated by the EPA (less than or equal to 5 ppb for TCE) a challenging problems.

Recent legislation regulating the disposal and cleanup of such hazardous wastes has led to an ongoing search for new treatment techniques. However, many of the now-developed technologies are not cost-effective, nor are they easily implemented. For example, current technology for remediating volatile organic compounds is essentially limited to "pump-and-treat" methods. In such methods, as described, for example, by H. H. Russell et al. in *Remediation* 1:167 (1990), the plume is penetrated by a number of wells, the contaminated ground water is extracted from the wells and pumped to the surface, treated by one of a number of methods at the surface, and then either injected into the subsurface or discharged. The pump-and-treat approach is expensive to operate, however, and there is significant uncertainty in the ultimate level of decontamination, the time required to achieve significant decontamination, and the permanence of decontamination. See, e.g., C. C. Travis et al., *Environ. Sci. Technol.* 24:1464 (1990), and K. H. Baker et al., *Geomicrobiol.* 8:133 (1991). The main cause of these uncertainties is the highly heterogeneous nature of the subsurface medium, which creates preferential flow paths for the extracted fluids. Less permeable subsurface regions receive less remediation and remain as sources of residual contamination to recontaminate the cleaned up regions. Additionally, many methods other than the pump-and-treat technique cannot permanently clean up water contaminated with certain types of hazardous materials.

In situ microbial bioremediation of aquifers contaminated with volatile organic compounds has received increasing attention as an alternative to the pump-and-treat technique. It has the potential advantages that many common organic contaminants can be biodegraded to innocuous compounds by naturally occurring microorganisms, that it is a contaminant-destructive as opposed to a contaminant-relocative process, and that it is carried out in situ, obviating the need for disposal of the treated groundwater. Unfortunately, clear-cut proof that biodegradation of the undesired organic contaminant has taken place in an aquifer has been difficult to substantiate, even for TCE added in very small amounts to a very small, slow aquifer.

The usual approach to in situ bioremediation is to pump a suite of nutrients into the subsurface to stimulate the growth of indigenous bacterial populations. Such methods are described, for example, in the following references: K. H. Baker et al., *Geomicrobiol.* 8:133 (1991); J. T. Wilson et al., *Ground Water Monit. Rev.*, Fall 1986, at page 56; M. D. Lee et al., *CRC Crit. Rev. Environ. Control* 18:29 (1988); P. V. Roberts et al., *Ground Water* 28:591 (1990); L. Semprini et al., *Ground Water* 28:715 (1990); L. Semprini et al., *Ground Water* 29:239 (1991); L. Semprini et al., *Ground Water* 29:365 (1991); P. E. Flathman, *Ground Water Monit. Rev.* 9:105 (1989); and J. T. Wilson et al., *Appl. Environ. Microbiol.* 49:242 (1985). Ideally, the resulting increase in biomass causes the desired biodegradation at an acceptable rate. However, three complications arise: (1) heterogeneous permeability of the subsurface environment makes it difficult to deliver nutrients through the contaminated plume; (2) nutrient pumping often causes preferential growth near the injection wells and can lead to biofouling; and (3) the biotransformation of halogenated hydrocarbons is generally a cometabolic phenomenon.

In a recent field study, in situ methanotrophic bioremediation was evaluated in a shallow, semiconfined aquifer that was about 1.5 m thick and consisted of fine- to coarse-grained sands and gravel (P. V. Roberts et al., *Ground Water*, 28:591 (1990); L. Semprini et al., *Ground Water*, 28:715 (1990); L. Semprini et al., *Ground Water*, 29:239 (1991); L. Semprini et al., *Ground Water*, 29:365 (1991)). Dissolved methane and oxygen were injected into the aquifer in alternating pulses to stimulate the growth of indigenous methanotrophs. Monitoring wells were located at 1, 2.2 and 3.8 m and an extraction well was situated 6 m downstream from the injection well. After several weeks of gas injection, biostimulation of the aquifer was achieved, but the methane-oxidizing bacteria grew preferentially within 2 m of the injection well. When TCE (97 ppb and later 51 ppb) was then injected, along with more methane and oxygen, the maximum biodegradation attained within 2 m of the downstream travel was only 20–30%. This field study suggests that the periodic pumping of a limited supply of methane plus air as a method to replenish a spent biofilter, promotes localized methanotrophic bacterial growth. The more obvious replenishment method would be simply to inject additional bioreactor grown cells.

The present invention is directed to the aforementioned problem, i.e., the removal of potentially hazardous contaminants from fluids, and involves the use of bioremediation. Specifically, the invention is premised on the discovery that certain microorganisms capable of producing an enzyme which degrades one or more targeted contaminants may be grown in such a way as to maximize the production and intracellular stability of that enzyme or enzyme systems, and further that such catalytically active, intact microorganisms may be injected directly into a pool or flow of contaminated fluid to remove contaminants therefrom. The invention is particularly useful in eliminating a number of toxic halogenated aliphatic and various aromatic organic chemicals from groundwater and the approach can be applied to other types of contaminants such as metals or radionuclides. The invention may be used to treat a contaminant source as well as a flowing contaminated stream. The bioremediation process of the present invention may also be used to treat small volumes of large, moving plumes or may be translated into a larger-scale context.

OVERVIEW OF RELATED ART

In addition to the publications cited and summarized in the foregoing section, the following references relate to microbiological and other methods for removing contaminants from fluids.

U.S. Pat. No. 2,142,196 to Langdon describes in general terms a "trickling" filter system for removing dissolved and suspended materials from sewage or other waste material. The filter may involve biological conversion of the solid material in the effluent to a more easily processed form.

U.S. Pat. No. 3,979,283 to Prudom describes a method for degrading dichloro-diphenyl-trichloroethane (DDT) using microorganisms which break down the DDT directly and convert it into a proteinaceous mass.

U.S. Pat. No. 4,664,805 to Focht relates to the use of nonindigenous microorganisms to degrade halogenated organic compounds. The disclosed method involves the use of a nontoxic analog of the targeted halogenated organic contaminant in combination with the microorganisms in order to support their growth.

U.S. Pat. No. 4,725,357 to Downing et al. describes a method for removing dissolved selenium from water which involves the use of a microbial biomass capable of reducing any selenium which may be present, and thereby converting the selenium to a form which can be captured or entrained by larger particles.

PCT Publication No. WO89/09827, inventors Winter et al., describes a method for degrading trichloroethylene by treating a trichloroethylene-containing sample with *Pseudomonas mendocina* KR-1 (PmKR1) or *Pseudomonas putida* Y2101, or with genetically engineered microorganisms which contain the PmKR1 toluene monooxygenase genes.

PCT Publication No. WO90/01465, inventors Valo et al., describes a process for the microbiological purification of water contaminated with chlorophenols. The invention involves the use of microorganisms such as Rhodococcus CP-2 and *Rhodococcus chlorophenolicus* PCP-1 which are stated to produce an enzyme which degrades the targeted contaminants.

Madsen, *Environ. Sci. Technol.* 25(10):1663–1673 (1991), Keeler, R&D Magazine (July 1991), p. 34–40, Abelson, *Science* 246(4934):1097 (December 1989), and Thayer, *Chemical & Engineering News* (Aug. 26, 1991), pp. 23–40, all relate to the use of bioremediation in addressing the problem of hazardous waste. Russell et al., *Remediation* 1(2):167–183 (winter 1990/91), specifically addresses the issue of trichloroethylene contamination, while Jeffers, California Geology (July 1991) pp. 154–158, is directed to the use of microorganisms to recover metals from waste.

SUMMARY OF THE INVENTION

Accordingly, it is a primary object of the present invention to provide a method for purifying contaminated fluid such as subsurface groundwater to remove a microbiologically degradable organic contaminant therefrom.

It is another object of the invention to provide such a method in which the fluid to be treated is contacted with an intact microorganism or a select suite of resting-state intact microorganisms capable of producing an enzyme or enzymes which degrade the contaminant.

It is still another object of the invention to provide such a method in which, prior to contacting the contaminated fluid with the microorganism, the microorganism is grown under conditions which optimize the amount of enzyme produced and simultaneously result in significantly augmented levels of whole-cell biodegradative catalytic activity and increased intact cell enzyme longevity.

It is yet another object of the invention to provide such a method wherein the aforementioned enzyme-enriched microorganism or group of select microorganisms is utilized in the form of a biofilter.

It is a further object of the invention to provide such a method wherein the enzyme-enriched microorganism composition is directly injected into a contaminated source for a subsurface groundwater stream or plume.

It is still a further object of the invention to provide a versatile method wherein the microorganism is a methanotroph, a heterotroph, or any microorganism which has useful biodegradative or redox catalytic properties which can be optimized and stabilized by prior growth under carefully defined conditions for economical in situ contaminant treatment applications via intact cell injections.

It is another object of the invention to provide such a method useful for removing chlorinated aliphatic hydrocarbons such as chloroform, carbon tetrachloride, and trichloroethylene, as well as a number of petroleum-related aliphatic and aromatic volatile organic compounds from a contaminated fluid.

It is still another object of the invention to provide such a method wherein the contaminant to be removed is a metal or a radionuclide.

Additional objects, advantages, and novel features of the invention will be set forth in part in the description which follows, and in part will become apparent to those skilled in the art upon examination of the following, or may be learned by practice of the invention.

In a first aspect, the invention provides a method for purifying subsurface groundwater to remove contaminants therefrom. This aspect of the invention is premised on the discovery that certain microorganisms produce enzymes which can degrade organic and other contaminants, and may be cultured in such a way as to optimize enzyme production and intact cell enzyme longevity. Methanotrophs, which are ubiquitous aerobic bacteria that can be cultured on methane as a sole carbon source, have been found to be particularly useful; methane monooxygenases ("MMOs") produced by methanotrophs have been found to exhibit oxidative activities with a broad range of organic substrates. With TCE in particular, methanotrophs degrade the contaminant very quickly. While not wishing to be bound by theory, it is postulated that such degradation occurs by biotransformation of TCE to the corresponding epoxide, which is highly reactive and rapidly hydrolyzed in aqueous systems.

In another aspect of the invention, the aforementioned method involves a treatment step in which the production of contaminant-degrading enzyme by the selected microorganism is enriched.

In yet another aspect of the invention, an enzyme-enriched microorganism is provided.

DETAILED DESCRIPTION OF THE INVENTION

I. Definitions

Figure 1:
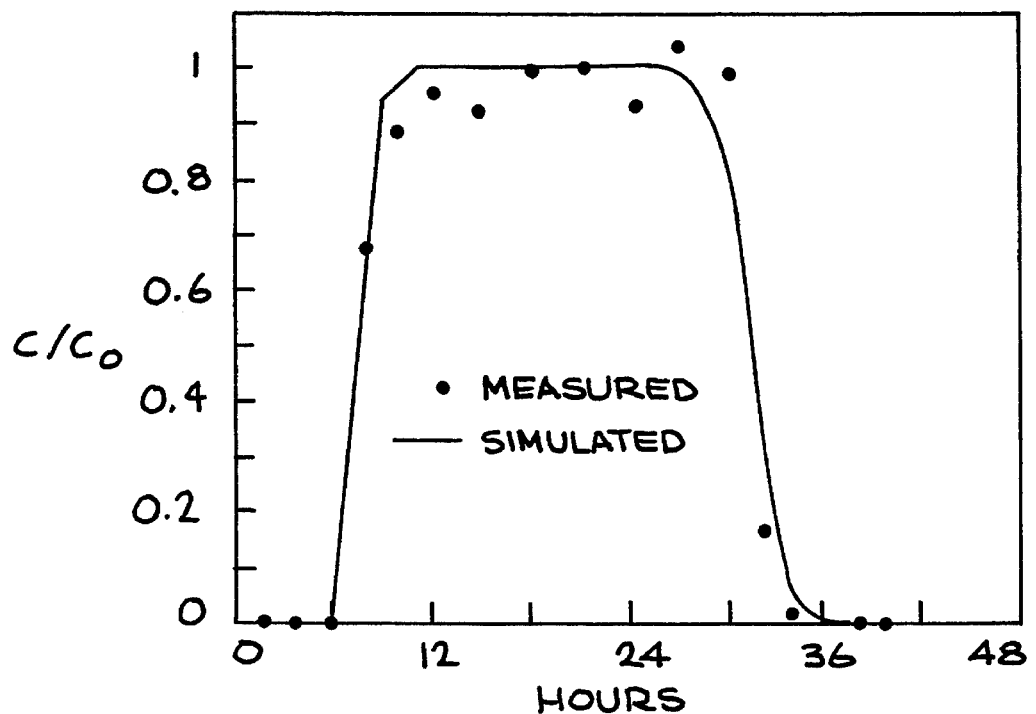
FIG. 1 shows measured experimental and simulated data (for no biodegradation) of the TCE wave at the sampling port in the 1.1-m test bed immediately upstream from the microbial filter, approximately 0.26 m from the bottom of the sand pack. $C/C_0$ is the concentration relative to the input 109-ppb TCE pulse. Travel time shown on the abscissa in this and subsequent figures is relative to the start of flow for a TCE wave; it can be related to position via the 1.5-cm/h flow velocity.

Before describing the present invention in detail, it is to be understood that this invention is not limited to the particular cell culture and enzyme-enrichment techniques described, or to particular field implementation methods use to emplace the biofilter, or the like, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a microorganism" includes a mixture of different microorganisms, reference to a method of using "the enzyme-enriched microorganism composition" includes a method of using one or more such compositions, reference to a contaminant being "an organic material" includes reference to a contaminant of one or more such materials, and the like.

In this specification and in the claims which follow, reference will be made to a number of terms which shall be defined to have the following meanings:

The term "purify" as used herein means the removal of greater than 75%, preferably greater than 90% and more preferably greater than 99%, of aqueous contaminants as defined herein.

The terms "enzymatically degradable" and "microbiologically degradable" are used interchangeably herein to mean the capacity of a contaminant to be degraded by enzyme-catalyzed biotransformation to innocuous, non-toxic compounds.

The terms "intact cells" or "whole cells" are used herein to mean viable cells which are metabolically active or capable of metabolic activity and which are capable of excluding vital stains.

The terms "intact resting-state cells" or "whole resting-state cells" is intended to mean viable cells which are capable of development, division and subsequent logarithmic growth but are captured in a phase in which cell division in culture is slowed or stopped by, for example, limiting the supply of an essential nutrient or nutrients, by depriving the cells of essential protein growth factors, by adding low levels of protein-synthesis inhibitors, or by allowing the cells to become overcrowded.

The term "intracellular longevity" is herein defined to mean resting-cell storage stability, as measured by the whole-cell activity half-life, of an intracellular constituent of interest. An "increased intracellular longevity" of an cellular enzyme as measured in a resting-state cells is thus an increase in the activity half-life of the enzyme.

The term "enzyme-enriched" to describe the intracellular amount or activity of an enzyme is used herein to indicate a proportionally greater amount or activity of an enzyme relative to either the non-enriched amount or activity of the enzyme or to other enzymes whose amount or activity may serve as a reference.

"Classical spontaneous or induced mutation and selection methods" are those procedures well known to those skilled in the art (see, e.g., the series, *Methods In Enzymology*, S. Colowick and N. Kaplan eds., Academic Press, Inc.).

"Halo" or "halogen" refers to fluoro, chloro, bromo or iodo, and usually relates to halo substitution for a hydrogen atom in an organic compound. Of the halos, fluoro and chloro are generally preferred.

The term "approximately" as used herein to describe, for example, pH values, solution concentrations, or the like, is intended to mean within 10 percent, preferably within 5 percent and more preferably within 2 percent. Thus, a pH of "approximately 7.0" is intended to mean a pH in the range of 6.5 to 7.5, preferably within the range of 6.75 to 7.25, and more preferably within the range of 6.9 to 7.1.

II. Overview of the process

The in situ bioremediation of aquifers contaminated with volatile organic compounds, metals and/or radionuclides offers the advantage that many common organic contaminants can be degraded to innocuous compounds by naturally occurring microorganisms. Typically, in situ bioremediation of contaminated aquifers is facilitated by injecting a suite of common nutrients into the subsurface to stimulate the growth of indigenous bacterial populations. However, growth stimulation by nutrient pumping does not necessarily enhance the numbers of useful contaminant degrading microorganisms to a sufficient degree because it is not a highly selective process. In addition, use of the nutrient pumping method of bioremediation often causes biofouling due to preferential bacterial growth near the injection wells.

Furthermore, when the contaminant is a chlorinated aliphatic hydrocarbon contamination, nutrient pumping can hinder the desired biodegradation due to the phenomenon of cometabolism.

Cometabolism is the fortuitous microbial transformation of anthropogenic compounds such as chlorinated hydrocarbons, and even metal ions, by intracellular enzymatic systems that are produced for other natural physiological purposes. Cometabolism usually cannot provide the carbon or energy required for cell growth. Thus, supplying nutrients to the subsurface to stimulate microbial growth often interferes with or competitively inhibits biodegradation of the trace contaminant concentrations (ppb to low ppm levels) of concern. This is certainly the situation for methanotrophic bacteria which grow on methane gas as a carbon source by producing intracellular methane monooxygenases (MMOs), since these enzymes are also the fortuitous biocatalyst systems that degrade compounds such as chloroform and trichloroethylene. Consequently, the growth substrate, methane, inhibits whole-cell methanotrophic chlorinated hydrocarbon biodegradation. In addition, for both methanotrophs and other types of aerobic (oxygen-requiring) bacteria, the stimulation of growth by the introduction of nutrients consumes dissolved oxygen that is essential for the oxidative transformations of most organic contaminants.

As an alternative to the above nutrient pumping approach, based on nutrient growth stimulation, this invention involves the use of resting (i.e., non-dividing) cells in an in situ microbial filter strategy. In this strategy, microorganisms are injected into the subsurface ahead of migrating contaminant plumes or at various points within the plume. The cell inocula for initially creating the microbial filter and periodically replenishing it are obtained from surface bioreactors in which the microorganisms have been grown under carefully managed conditions with respect to the culture medium, pH, temperature, oxygenation, etc. The inocula, derived from such surface bioreactors, can be either a single pure bacterial strain or else a mixture of bacteria that collectively possess the desired contaminant degradation properties. A portion of the injected microorganisms attach to the soil or rock and form a zone of enhanced biodegradation activity (i.e., the in situ microbial filter). Contaminated groundwater flows into this zone, the attached microbial population biodegrades the contaminant at a rate that keeps pace with its rate of transport, and the groundwater exits clean. Such a strategy also allows for and includes the concurrent treatment of the contaminant source by microbial inoculation and for the possible emplacement of multiple microbial filters across the expanding dimension of a contaminant plume to accelerate the remediation process. This combined in situ microbial filter plus source treatment approach is based, in part, on techniques that have been employed for microbial enhanced oil recovery (E. C. Donaldson et al., *Microbial Enhanced Oil Recovery*, Elsevier Press (1989)).

III. Process details

For in situ microbial filter applications that are focused on volatile organic compounds, particularly chlorinated aliphatic organic compounds (e.g., chloroform, trichloroethylene), the primary preferred bacteria to be utilized are obligatory methanotrophs belonging to the genus Methylosinus, strain trichosporium, although a number of other microorganisms capable of enzymatically degrading volatile organic materials can be used as well. Methanotrophs are naturally occurring, aerobic, nonpathogenic bacteria which are found ubiquitously throughout the world in aerated soils and waters that contain methane. Obligatory methanotrophic bacteria derive both their biomass and their energy for growth from the uptake and oxidation of methane as a sole carbon source. They have been isolated in a number of research laboratories and some strains are also available from national culture collections. The sub-strain *M. trichosporium* OB3b was originally isolated about 22 years ago by Whittenbury et al., *J. Gen. Microbiol.* 61:2025 (1970), but has since been distributed to and studied by a number of investigators. When cultured so as to produce the soluble form of its methane monooxygenase (sMMO) as opposed to the particulate (membranous) form of its monooxygenase (pMMO), strains of *M. trichosporium* can oxidatively transform and hence have the potential to bioremediate a large collection of volatile organics. This potential arises due to the broad substrate range exhibited by *M. trichosporium* sMMO enzyme systems. The substrate range includes short chain halogenated alkanes and alkenes, aromatics in the BTEX group, naphthalene, simple ethers and some pyridines.

A primary focus of this invention is on the application of a selected methanotroph in a subsurface microbial filter configuration created by injecting prior cultured *M. trichosporium* OB3b cells. However, the invention strategy is equally applicable to heterotrophic or other types of microorganisms, including but not limited to bacteria and yeast, that could be chosen for their abilities to transform other organic contaminants, to reduce and, thereby, directly precipitate certain metal ions such as those of Fe, Pb, Se, Te, Mo, Cr, U, and Pu, and to generate sulfide from sulfate or nitride from nitrate and, thereby, indirectly effect the removal of a wide array of heavy metals as their insoluble sulfide or nitride compounds. In the application of microorganisms (other than methanotrophs of the genus Methylosinus) via the invention's microbial filter strategy, it is understood that for each selected strain the surface bioreactor culturing conditions would have to first be studied to optimize the chosen metabolic contaminant transformation function per unit of cell mass and to maximize the longevity of this activity in intact cells. An example of such an optimization-maximization is described and claimed for *M. trichosporium* OB3b below.

An important feature of this invention is the establishment of a resting cell, bioactive, contaminant-degrading zone (in situ microbial filter) by introducing a selected microorganism or set of microorganisms that have been previously cultured in a bioreactor under carefully defined conditions. The invention fosters the creation of a thin in-place, subsurface bioremediation reactor via the injection of washed pre-cultured microorganisms which serve as carriers of specific enzyme catalysts that are active in ambient in situ environments. Periodic biofilter replenishment will be primarily by the injection of additional fresh cells, perhaps secondarily by intermittent limited single nutrient additions (e.g., methane gas). Simultaneous source treatments are also emphasized, again using pre-grown, resting cells as the enzyme catalyst carrier.

With respect to the specific methanotroph, *M. trichosporium* OB3b, a bioreactor culturing procedure has been devised that results in a high yield of biomass in which the whole-cell (intact-cell) sMMO activity has been optimized and its longevity (resting-cell storage-stability) has been maximized or at least greatly extended. Optimizing an intact cell's catalytic activity and maximizing its longevity for transforming or degrading the contaminant of concern are pivotal to the success and economic feasibility of the resting cell in situ microbial filter strategy of the invention.

IV. Field Implementation

The invention may be practiced in at least two types of field implementations: via a trench and via wells. The trench application is restricted to contaminant plumes with relatively shallow depths. Briefly, a trench or trenches are dug perpendicular to the primary direction of migration of the contaminant plume. The trench is filled with porous material, e.g., sand, by standard means which include the trench being filled as it is being dug. Either horizontal or vertical wells are emplaced into the trench and these are used to inject microbes into the porous medium. The success of the remediation may be measured by monitoring contaminant concentrations entering the trench and comparing these with concentrations leaving the trench.

For deeper contaminant plumes, wells may be used to deliver (inject) the microbes to a narrow, nearly vertical volume transecting the main flow direction. These wells can be either horizontal or vertical, depending on the nature of the vertical permeability as it occurs naturally in the subsurface. The wells can be used to inoculate the subsurface by some combination of injection and withdrawal cycles or alternating injection and withdrawal wells. The success of the remediation can be measured by monitoring contaminant concentrations entering the volume of enhanced microbial activity and comparing these with concentrations leaving the volume of enhanced microbial activity.

Experimental

The following experimental material is intended to provide those of ordinary skill in the art to which the invention pertains with a complete disclosure and description of how to implement the method of the invention, and is not intended to limit the scope of what the inventors regard as their invention in any way. Other aspects, advantages and modifications within the scope of the invention will be apparent to those skilled in the art. Efforts have been made to ensure accuracy with respect to numbers used (e.g., amounts, temperatures, etc.), but some experimental error and deviation should, of course, be allowed for. Unless indicated otherwise, parts are parts by weight, temperatures are in degrees celsius, and pressure is at or near atmospheric.

To test this biofilter strategy in the laboratory, a meter-scale test bed was developed. The internal dimensions of the frame containing the test bed were 1.1 m in length, 0.4 m in height, and 0.1 m in width. Flow of water in the test bed was horizontal, along the long dimension, and was strictly one-dimensional. Except for three glass inspection windows, the inside surfaces of the frame were nickel metal, mostly pure nickel foil covering nickel-plated stainless steel. The frame was filled with water and then with a commercially available sand. It was a high-purity quartz sand with trace amounts of hematite, illite and calcite. The grain size distribution was narrow, with 84% of the grains having a diameter between 0.106 and 0.25 mm. The sand pack was completely saturated (no visible gas bubbles), and had a bulk permeability of approximately 8.5 Darcys and a porosity of 0.34±0.02. Once the test bed was sealed, a horizontal flow of 10 mM Higgin's phosphate buffer (S. Park et al., *Biotech. Bioeng.*, 38:423 (1991); S. Park et al., *Biotech. Bioeng.*, in press (1992); N. N. Shah et al., *Biotech. Bioeng.*, submitted (1992)) was initiated and maintained at a constant rate of 200 mL/h (flow velocity ~1.5 cm/h, a typical value for the flow of natural groundwater). The disclosures of the aforementioned references are hereby incorporated by reference.

A colored tracer (phenol red) and time-lapse photography through the glass windows revealed a 25% increase in permeability from the top to the bottom of the test bed, but the increase was roughly constant, without any undesirable "fingering" of flow, for example. Tracer tests also showed convincingly that there were no permeability gradients in the horizontal plane and that there were no short circuits for flow through the bed.

Fluids within the wet sand pack were sampled through side-wall ports attached to the ends of porous, 6-mm outer diameter, thick-walled fritted nickel tubes that extended across the full 0.1-m width of the sand pack. The nickel tubes had roughly the same porosity and permeability as the sand pack and a pore size of approximately 20 μm. Tracer tests demonstrated that fluids taken from the ports were sampled uniformly across the sand pack.

Bacteria ($4.7 \times 10^9$ cells/ml) were injected into the sand test bed through a column of 5 sampling ports approximately 0.2 m from the inlet port at a rate of 2 ml/min/port using a peristaltic pump. Fluid was simultaneously removed, at 1 ml/min/port, from the columns of 5 ports located approximately 0.15 m and 0.25 m from the inlet port, with a second peristaltic pump, to establish a closed circulatory system. The peristaltic pumping directions were then reversed and the zone between the second and fourth column of ports was flushed with 10 mM Higgin's medium phosphate buffer (pH 7.0) to remove the unattached cells. During bacterial injection and withdrawal procedure, the ambient flow field was stagnant. From the difference between the number of cells injected and the number withdrawn, the number of bacteria that initially attached in the zone was determined to be $1.6 \times 10^{12}$. Establishment of the microbial zone and all of the subsequent flow-through experiments were carried out at 21°–22° C. in a temperature-controlled room.

*Methylosinus trichosporium* OB3b was selected as the prototype methanotroph for these tests for several reasons. First, it is one of the two best-characterized methane-oxidizing bacterial strains currently available. Second, it can be easily grown in bioreactors at 30° C. (doubling-time ~7 h) to yield high densities of bacteria that contain only the soluble form (sMMO), as opposed to the membranous particulate form (pMMO) of intracellular methane monooxygenase (S. Park et al., *Biotech. Bioeng.*, 38:423 (1991); S. Park et al., *Biotech. Bioeng.*, in press (1992); N. N. Shah et al., *Biotech. Bioeng.*, submitted (1992)). Third, *M. trichosporium* OB3b cells producing sMMO are among the most active methanotrophs with respect to TCE biodegradation catalysis (H.-C. Tsien et al., *Appl. Environ. Microbiol.*, 55:228 (1989); R. Oldenhuis et al., *Appl. Environ. Microbiol.*, 55:2819 (1989); G. A. Brusseau et al., *Biodegradation*, 1:19 (1990); R. Oldenhuis et al., *Appl. Environ. Microbiol.*, 57:7 (1991)).

In related experiments, fresh cells containing sMMO convert propene to propene oxide at rates of 100–150 nmol/min/mg dry cell wt at 30° C. in the presence of 20 mM formate as an electron donor (S. Park et al., *Biotech. Bioeng.*, 38:423 (1991); S. Park et al., *Biotech. Bioeng.*, in press (1992); N. N. Shah et al., *Biotech. Bioeng.*, submitted (1992)). With 0.5 μmole of unlabeled or [1,2-$^{14}$C]TCE (2,000 cpm/nmol) substituted for propene in the same standard assay mixture (S. Park et al., *Biotech. Bioeng.*, 38:423 (1991); S. Park et al., *Biotech. Bioeng.*, in press (1992); N. N. Shah et al., *Biotech. Bioeng.*, submitted (1992)), the initial steady-state rate of biotransformation (measured either by TCE disappearance or the appearance of nonvolatile water-soluble radioactive products) is routinely 40–60 nmol/min/mg dry cell wt. Whole-cell biodegradation of TCE by *M. trichosporium* is decidedly a catalytic property of the sMMO as opposed to the pMMO (H.-C. Tsien et al., *Appl. Environ. Microbiol.*, 55:228 (1989); R. Oldenhuis et al., *Appl. Environ. Microbiol.*, 55:2819 (1989); G. A. Brusseau et al., *Biodegradation*, 1:19 (1990); R. Oldenhuis et al.,

*Appl. Environ. Microbiol.*, 57:7 (1991)). The TCE biotransformation rate for cells containing sMMO is 75–100 times faster than for cells containing pMMO, under both saturating and limiting concentrations of the TCE substrate.

The *M. trichosporium* OB3b cells are batch cultivated in a stirred bioreactor at 30° C. pH 6.8–7.2, with a 3:1 (vol/vol) 10% $CO_2$-containing air:methane gas mixture in Higgin's minimal nitrate salts medium (Cornish et al., *J. Gen. Microbiol.* 130:2565 (1984)) lacking $CuSO_4.5H_2O$, but fortified with approximately 2× $FeSO_4.7H_2O$ and approximately 2× $NaNO_3$ (Park et al., *Biotechnol. Bioeng.* 38:423 (1991)) ("minus $CuSO_4$ Higgin's medium"). It will be recognized by those skilled in the art that, although $CuSO_4.5H_2O$ is the Cu-salt component of Higgin's minimal nitrate salts medium, it is the Cu availability which is the factor governing the location or form of the methane monooxygenase in methanotrophs. These conditions were devised at the Lawrence Livermore National Laboratory for obtaining cells that produce exclusively intracellular sMMO at biomass densities about 2.5 g dry cell weight per liter of medium. Cell densities in the bioreactor were continuously monitored by measuring the absorbance at 660 nm $A_{660}$ of the culture broth pumped into a flow-through cell positioned in a spectrophotometer.

Further modifying the minus $CuSO_4$ Higgin's medium by raising the $NaMoO_4.2H_2O$ approximately 40× to about 16 micromolar and including $NiCl_2$ at approximately 7.5 micromolar will markedly enhance the resting-cell-state functional longevity of this sMMO for trichloroethylene biodegradation. To maximize this whole-cell sMMO activity, the cells are grown in this further modified, $NiCl_2$-supplemented medium until depletion of its nitrate occurs after about 80–100 hours of culturing, depending on the precise inoculum cell density. The usual inoculum density corresponds to $A_{660}$=0.03–0.04. When complete nitrate depletion is reached as determined with an ion-specific electrode, additional approximately 1× amounts of $FeSO_4.7H_2O$ and $MgSO_4.7H_2O$ are added to the bioreactor cultures. As nitrate depletion occurs, the cells display a transition from a fast (6–7 hour doubling time; specific growth rate (μ) approximately 0.08 $h^{-1}$) to a much slower growth rate (μ approximately 0.008 $h^{-1}$). At the end of this transition stage (after about 95–120 total hours of bioreactor culturing), the final cell density was about 2 to 5 g dry cell weight/L culture broth. The cells are then harvested by centrifugation, washed and stored as a resting-cell (non-dividing) suspension in 10 mM Higgin's phosphate buffer, pH 7.0.

Freshly prepared *M. trichosporium* OB3b cells generated in the foregoing manner convert propene (a surrogate substrate for methane) to propene oxide at rates of 100–150 nmol/min/mg of dry cell weight and they oxidize trichloroethylene at rates of 40–60 nmol/min/mg dry cell weight at 30° C. under steady-state conditions and in the presence of 20 mM formate added as an electron donor. *M. trichosporium* OB3b prepared as described above exhibit a whole-cell sMMO-activity half-life for trichloroethylene degradation of about 35 days, compared to a longevity half-life of only about 3 days if the cells are cultured as customary in standard Higgin's medium and then harvested during the logarithmic growth phase.

While not wishing to be bound by theory, the inventors herein propose that the biochemical basis for this enhanced whole-cell catalytic longevity is the depletion of the culture medium nitrate in the presence of appropriate amounts of certain metal ions. The nitrate depletion may be linked to the induction of nitrogenase and hydrogenase activity, coupled with the intracellular accumulation of carbonaceous energy storage material such as poly-b-hydroxybutyrate within the cells, i.e., during the late part of the growth shift transition stage. The efficacy of the method for producing *M. trichosporium* OB3b cells with both high resting-state sMMO catalytic activity and enhanced catalytic longevity on cell storage appears to be the result of several factors. Growing the cells in minus $CuSO_4$ Higgin's medium results in the exclusive expression of soluble (as opposed to particulate) methane monooxygenase. Raising the Higgin's medium Fe and nitrate concentrations approximately two-fold increases the cell density at which cells shift from a fast to a slow- or no-growth phase. Increasing the Fe in this manner also yields a higher cellular sMMO catalytic activity at this growth rate-transition phase. Thus, at the growth rate-transition phase, these modifications of the growth medium result in higher cell density and greater sMMO activity per unit of final biomass density. Raising the Mo concentration and including Ni in the culture medium results in cells which can fix dissolved $N_2$ and that can use $H_2$ gas as an electron source. Whole cell nitrogenase (an Fe/Mo-containing enzyme) and hydrogenase (a Ni-containing enzyme) activities can be detected in *M. Trichosporium* OB3b cells grown under the above-described conditions. Due to this ability to fix $N_2$, when cells deplete medium nitrate, they do not undergo a complete nitrogen starvation but continue to grow slowly beyond 80 hours. The additional source of electrons due to the ability to utilize $H_2$ further drives the MMO system. The addition at approximately 80 to 100 hours of cell growth of approximately 1× amounts of Fe and Mg, which have by then become depleted from the culture medium, is required not only for the expression of sMMO activity (Fe is part of the sMMO catalytic site) but also for continued cell growth beyond 80 hours (Mg is required for the activity many enzymes required for cell growth). Consequently, the harvested resting-state cells have sMMO enzyme, nitrogenase which allows the cells to fix dissolved $N_2$, and an additional source of electrons to drive the MMO system (each molecule of dissolved $N_2$ that is fixed into ammonia yields a molecule of hydrogen).

Irrespective of the mechanism(s) involved, this whole-cell sMMO longevity is a significant factor in the success of the microbial filter strategy of this invention for the in situ biodegradation of trichloroethylene and other volatile organic contaminants.

Biodegradation Experiments

Figure 2:
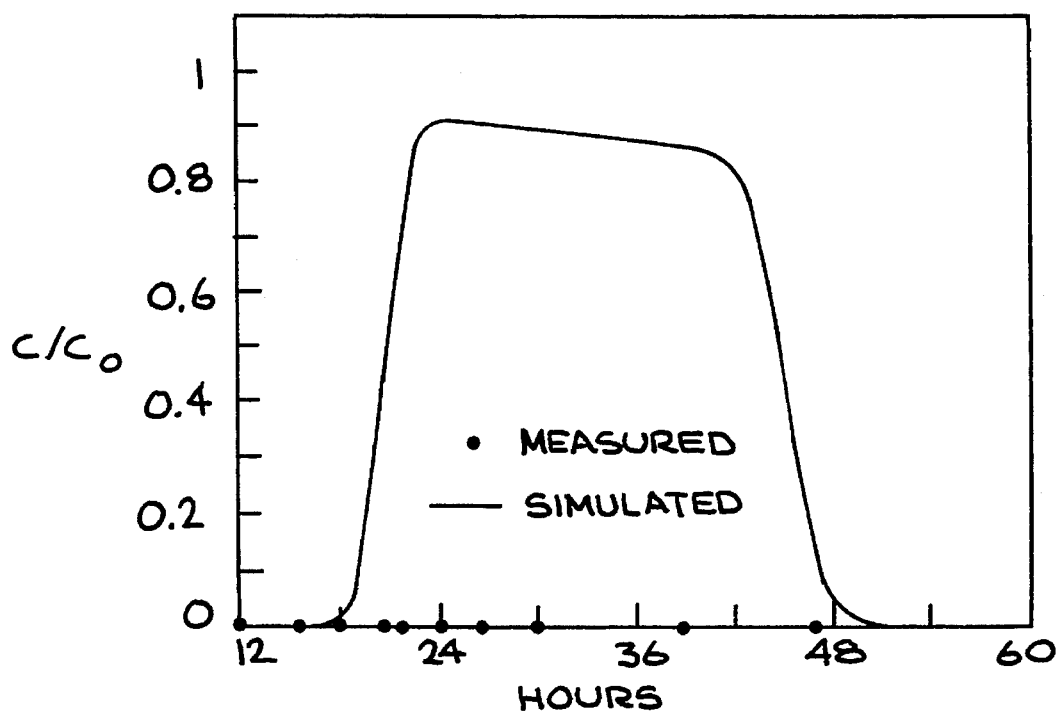
FIG. 2 shows measured experimental and simulated data (for no biodegradation) of the TCE wave at the sampling port immediately downstream from the microbial filter, approximately 0.26 m from the bottom of the sand pack. $C/C_0$ is defined as in FIG. 1.
Figure 3:
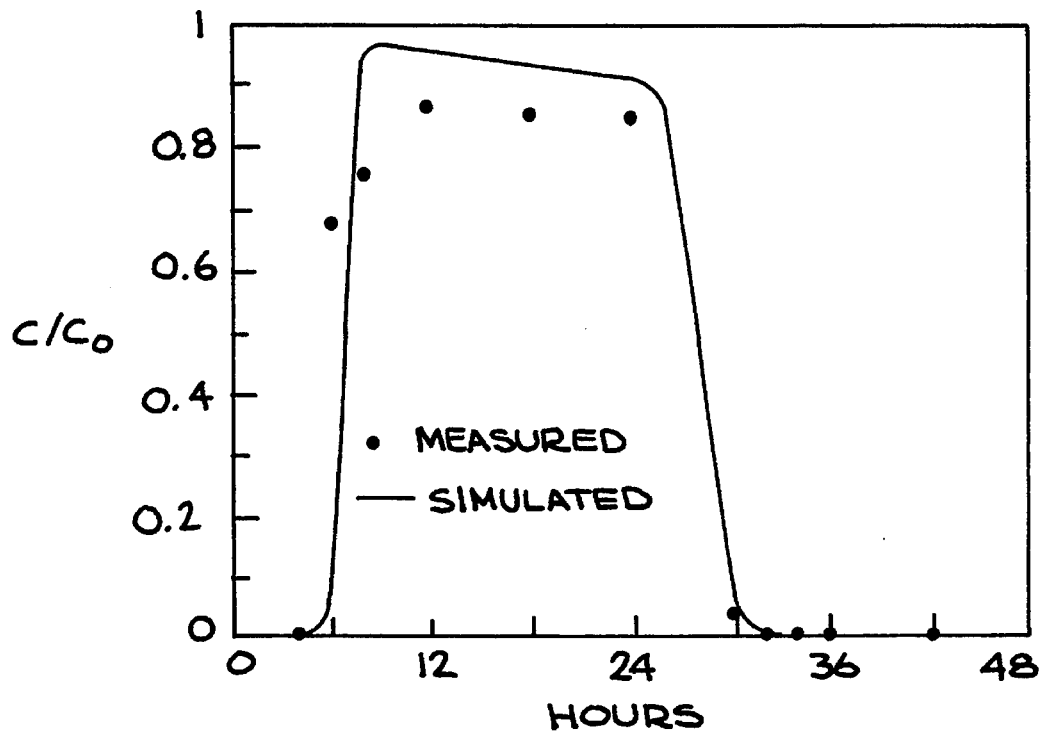
FIG. 3 shows measured experimental and simulated data (for no biodegradation) of the TCE wave at the sampling port immediately upstream from the microbial filter, approximately 0.14 m from the bottom of the sand pack. $C/C_0$ is the concentration relative to the input 85-ppb TCE pulse.
Figure 4:
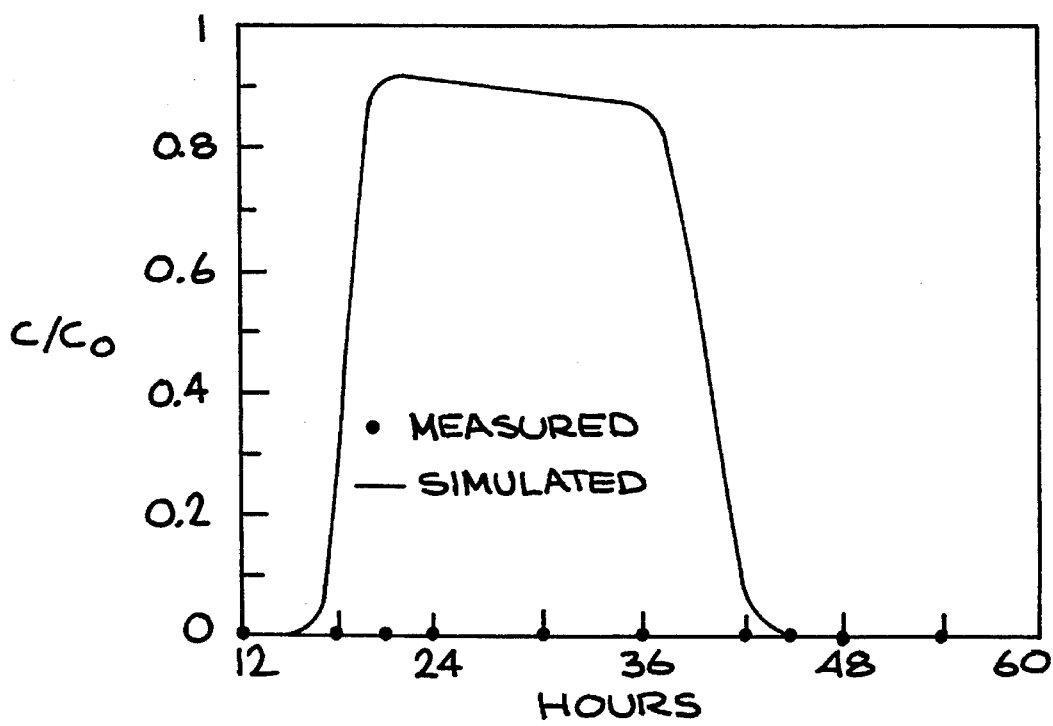
FIG. 4 shows measured experimental and simulated data (for no biodegradation) of the TCE wave at the sampling port immediately downstream from the microbial filter, approximately 0.14 m from the bottom of the sand pack. $C/C_0$ is as defined in FIG. 3.

At the start of the experiments, *M. trichosporium* OB3b bacteria, which had been batch-cultured in a 5-L bioreactor to produce sMMO, were harvested by centrifugation, washed, and resuspended in Higgin's phosphate buffer (pH 7.0). As detailed above, the cells were then pumped into the test bed to create an attached biofilter that was about 0.1 m thick in the flow direction. Cell-count-balance data revealed that 9% of the injected bacteria attached to the sand. After this inoculation, a 24-hour pulse of TCE (523 μg) at a concentration of 109 ppb in Higgin's phosphate was pumped into the test bed at the inlet port. Analyses by gas chromatography of 1-mL aliquots withdrawn from ports immediately ahead of the emplaced microbial filter showed the arrival of the TCE pulse (FIG. 1), whereas no TCE was detected immediately downstream of the filter (FIG. 2). The expected TCE arrival times for no TCE biodegradation were simulated by using a one-dimensional mathematical model for advective-dispersive transport in a porous medium with linear equilibrium sorption (H. S. Carslaw and J. C. Jaeger, *Conduction of Heat in Solids*, Clarendon Press (1959)). The data in FIGS. 1 and 2 indicate complete biodegradation of the TCE pulse (>99%). The experiment was repeated 7 days later with a second 24-hour TCE pulse (316 μg) at a concentration of 85 ppb, pumped through the originally emplaced microbial filter. The result was comparable to that of the first experiment in that no TCE could be detected downstream of the biofilter (FIGS. 3 and 4).

Figure 5A:
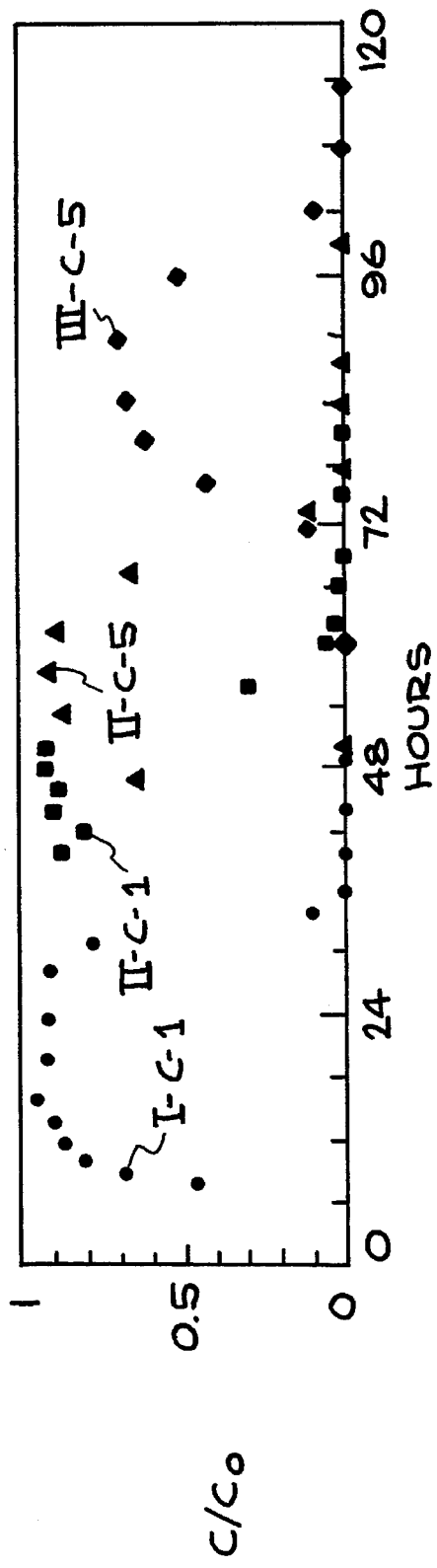
FIG. 5 shows a comparison of the TCE mass balance data from the control experiment (469 μg pulse), generated prior to the injection of bacteria, with the data from the first biofilter experiment collected following establishment of the microbial filter zone. Data are from samples taken along the length of the 1.1-m test bed, approximately 0.2 m from the bottom of the sand pack. The port at location I-C-1 is approximately 0.1 m from the inlet port; the other locations, all with respect to the inlet are: II-C-1, ~0.45 m; II-C-5, ~0.65 m; and III-C-5, ~0.99 m. The emplaced microbial filter was located between 0.16 and 0.25 m.
Figure 5B:
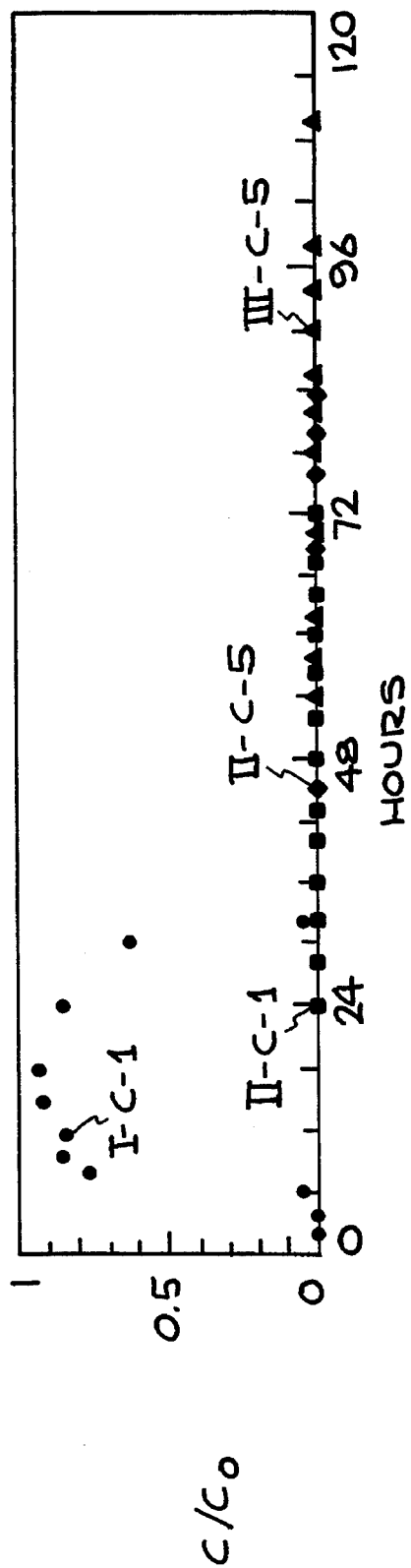

These two biofilter experiments were preceded by two mass-balance control experiments in which 24-hour, ~100-ppb pulses of TCE were passed through the test bed before the *M. trichosporium* OB3b cells were introduced. The sequential appearance of the TCE pulse at each port of the row 0.2 m from the bottom of the sand pack along the entire 1.1-m length of the test bed is in vivid contrast to the quantitative removal of the TCE pulse by the attached microbial filter (FIG. 5). Total recoveries of TCE at the outlet for the two mass-balance control experiments were 76 and 84%, respectively.

Permeability measurements of the sand pack were made before the TCE mass-balance control experiments and again after the experiments with the emplaced biofilter. During this interval of approximately 6 weeks, fluid had been flowing continuously through the test bed, except during inoculation. No measurable change in permeability was observed, confirming the absence of any biofouling. Likewise, none was predicted, based on our calculations that in the microbial filter zone only 3% of the surface area of the sand grains were covered by the attached cells.

After the post-experimental permeability measurements, 17 days after the bacteria were emplaced, the test bed was disassembled and the sand pack was systematically sampled in the area approximately 0.1 to 0.3 m from the inlet port, which included the injected biofilter zone. The sand pack was sequentially excavated in six horizontal layers between the removable fritted nickel tubes. Ten wet sand samples per layer (each containing 2.1 g of dry sand were analyzed for their cell number and their steady-state [1,2-$^{14}$C]TCE bioactivity. These initial steady-state rate assays were performed at 30° C. in the presence of formate, by replacing propene with 0.5 μmole of [1,2-$^{14}$C]TCE (2000 cpm/nmol) in the standard (0.5 ml) whole-cell sMMO incubation mixture. The lower limit for measuring the rate of radiolabeled TCE degradation in these assays is 0.02 nmol/g/min. The attached cells were readily dislodged by shaking the wet sand samples for 30 seconds in 5 ml of Higgin's phosphate buffer. After allowing the sand particles to settle, aliquots of the suspended bacteria were removed for cell counting and [1,2-$^{14}$C]TCE activity assays. Measurements of the attached cell population and the remaining levels of whole-cell sMMO catalytic activity (for labeled TCE) were performed with these samples. The maximum attached cell population density was on the order of 108 cells/g of dry sand and the maxima were approximately centered around the column of ports at which they were injected; a small amount of downstream spreading can be inferred. The residual whole-cell sMMO activity averaged 0.2 nmol of TCE oxidized/min/g of dry sand; it was skewed somewhat downstream from the remaining attached bacterial population. This suggests some preferential loss of catalytic activity in the upstream portion of the microbial filter, where most of the TCE biodegradation likely occurred. No TCE or other volatile halogenated compounds were detected when representative samples of the sand pack from throughout the excavated test bed were heated to 60° C. and analyzed by gas chromatography.

These results and those presented in FIGS. 1–5 demonstrate that a microbial filter was established by injecting resting cells and that this filter removed ~100-ppb levels of TCE to below a detectable limit of 0.5 ppb. Yet TCE removal alone does not constitute proof that this contaminant disappearance is primarily due to *M. trichosporium* OB3b biodegradation.

Figure 6:
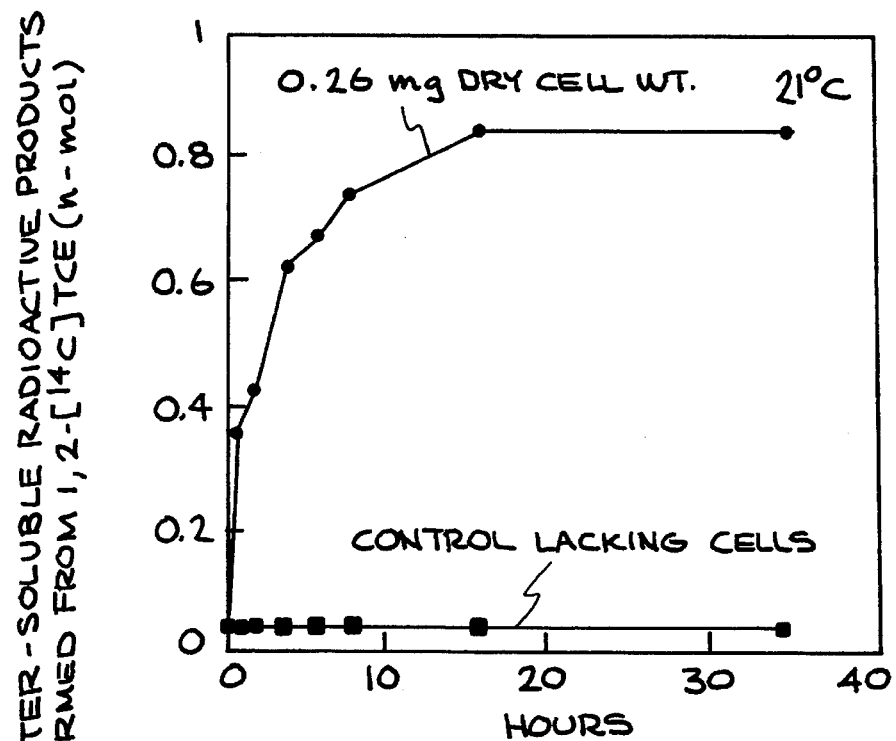
FIG. 6 depicts the time-course of whole-cell biotransformation of a [1,2-$^{14}$C]TCE concentration (131 ppb) similar to the unlabeled TCE pulses injected into the 1.1-m test bed for the biofilter experiments.

To address this point, an aliquot of the same cell suspension that was used to create the test bed microbial filter was stored 17 days at room temperature in Higgin's phosphate buffer (pH 7.0). Samples, each containing 5×10$^8$ cells, were then incubated in 1.0-ml volumes of Higgin's phosphate buffer with 1.0 nmol (131 ppb) of [1,2-$^{14}$C]TCE (4000 cpm/nmol) and the amount of bioconversion was determined at the times shown in FIG. 6. The resting-stage age of these cells was identical to that of the bacteria that earlier were attached to the sand pack and subsequently excavated and detached. The concentration of [1,2-$^{14}$C]TCE (131 ppb) was chosen to be similar to the previous test bed pulses of unlabeled TCE. Moreover, the total incubation period was selected to span the time required for a TCE wave to traverse approximately 0.2 m of the test bed. Approximately 80–85% of the [1,2-$^{14}$C]TCE was biotransformed to water-soluble products. About 10% of the radiolabeled TCE that was added to the control incubation vials could not be recovered from the organic phase; this may account for the apparently incomplete cellular conversion. At 17 and 35 hours, all of the water-soluble $^{14}$C-product material was nonvolatile (stable to freeze drying). A preliminary analysis of this mixture showed that it consisted of [$^{14}$C]bicarbonate, [$^{14}$C]formate and several other components. Also, a small amount of the added $^{14}$C (5–8%) was firmly associated with the cell pellet. Similar findings have been reported by others, when [1,2-$^{14}$C]TCE was incubated with either a mixed (M. M. Fogel et al., *Appl. Environ. Microbiol*, 51:720 (1986)) or pure (C. D. Little et al., *Appl. Environ. Microbiol*, 54:951 (1988); R. Oldenhuis et al., *Appl. Environ. Microbiol.*, 57:7 (1991)) methanotrophic culture.

Collectively, the data described above strongly support the view that virtually complete biodegradation of the TCE pulse in the test bed was effected by the microbial filter.

Scale-Up to Field Site

In contemplating a scale-up of the resting cell methanotrophic filter to a field site near the Lawrence Livermore National Laboratory ("LLNL"), a bioactive zone 50 m across, 5 m high, and 1 m thick was estimated to be adequate to capture a migrating contaminant plume. The aquifer water has a pH of about 7.5, an electrical conductivity and ionic strength about the same as 10 mM Higgin's phosphate buffer, and it contains TCE (~100 ppb) as the predominant contaminant. In planning such a scale-up, three fundamental considerations are significant with respect to the bacteria: the efficiency of bacterial attachment in the porous subsurface media, the longevity or stability of the whole-cell sMMO catalytic activity, and the absolute quantity of TCE that a given number or mass of cells can biotransform.

Figure 7:
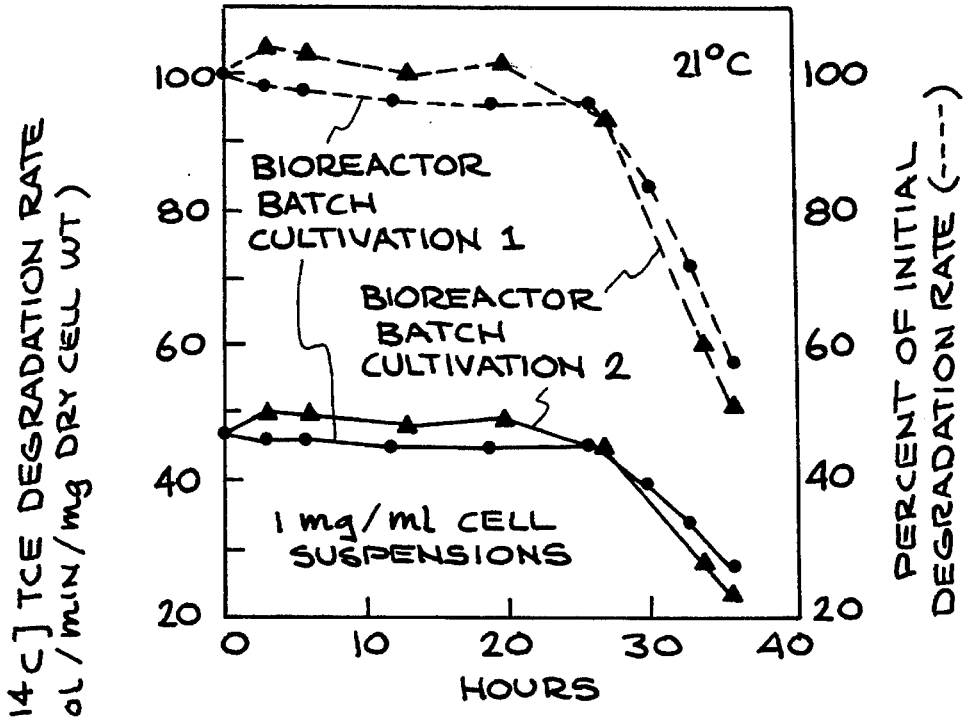
FIG. 7 shows the effect of resting-state cell storage of sMMO-containing bioreactor-grown *M. trichosporium* OB3b on whole-cell sMMO stability.

The bioreactor culture medium and cell harvest time have a profound influence on the subsequent sMMO longevity. FIG. 7 depicts the resting cell storage data for two separate batch cultivations. The cells were batch-cultivated in minus CuSo$_4$ Higgin's medium as described above, harvested and washed, and then stored in 10 mM Higgin's phosphate buffer (pH 7.0) as a 1.0 mg/ml cell suspension in stoppered 2-ml plastic tubes at room temperature. At the times shown, cell suspension samples were removed and assayed at 30° C. for their initial steady-state rates of [1,2-$^{14}$C]TCE (2000 cpm/nmol) biotransformation, in the presence of formate, by substituting 0.5 μmole of labeled TCE for propene in a standard whole-cell sMMO incubation mixture. If the cells are grown on standard Higgin's medium and harvested during the logarithmic growth phase, the whole-cell sMMO half-life is only ~3 days; if they are collected in the slow-growth phase, it is increased to ~6 days. But if they are cultured under modified conditions and harvested as described for the test bed experiments, the sMMO half life, using [1,2-$^{14}$C]TCE as the substrate, is greatly extended to ~35 days (FIG. 7).

Similar results have been obtained when the cells were cultured in the same manner and then stored in small tubes of buffer-saturated quartz sand. Although the cause of this markedly enhanced catalytic longevity is currently unknown, the consistent biphasic shape of the data (FIG. 7) suggests that the whole-cell sMMO is fully retained or spared, until some other intracellular component, perhaps NADH-regenerating or energy-yielding, is consumed. Thus, cells cultured by the methods described herein have improved whole-cell catalytic longevity.

From repeated exposures of *M. trichosporium* OB3b at 21° C. (no added formate) to 13.1 ppm of [1,2-$^{14}$C]TCE (2,000 cpm/nmol), with centrifugal reisolation of the cells for each successive addition, a finite transformation capacity of 0.24 mg/mg of dry cell weight (±0.03 s.d.) was found for three separate experiments. At an estimated flow of ~0.38× 106 L/day through the filter, the TCE load would be ~38 g/day. Using the bulk density of 1.69×103 kg/m$^3$ for the sand in the biofilter area and a *M. trichosporium* OB3b attached cell density of 1×10$^8$/g of sand, the filter biomass requirement would correspond to 25 kg. Based on a TCE capacity of 0.24 mg/mg of cell wt. this filter could, in principle, biodegrade the TCE flowing through the filter region for 158 days. Given these parameters, the lifetime of such a microbial filter for this particular field site would most likely be dictated by the longevity of the intracellular sMMO, the duration of microbial attachment, and additional factors. For plumes with greater TCE loading rates, however, the finite transformation capacity of the freshly cultured bacteria is a factor of comparable and perhaps dominant importance when compared to enzyme longevity and attachment duration. Findings with *M. trichosporium* OB3b indicate that the transformation capacity can be increased by at least twofold with the addition of an electron donor to facilitate more intracellular NADH regeneration.

What we claim is:

1. A method for purifying subsurface groundwater to remove certain enzymatically degradable contaminants therefrom, comprising the sequential step of:
   (A) providing a microorganism capable of producing an enzyme which allows the intact resting-state cells to degrade the contaminants;
   (B) growing the microorganisms under conditions which increase the amount and intracellular longevity of the enzyme, to produce an enzyme-enriched intracellular enzyme longevity-enhanced microorganism composition; and
   (C) contacting the subsurface groundwater with the enzyme-enriched, intracellular enzyme longevity-enhanced microorganism composition in a resting state;
   wherein the microorganism composition having increased whole-cell contaminant-degrading activity is prepared by the process comprising:
     (a) providing a microorganism capable of producing an enzyme which allows the microorganism in a resting state to enzymatically degrade organic materials;
     (b) providing a cell culture medium by modifying Higgin's minimal nitrate salts medium by omitting $CuSO_4 \cdot 5H_2O$ therefrom and adding approximately 2× $FeSO_4 \cdot 7H_2O$ and approximately 2× $NaNO_3$ thereto;
     (c) batch cultivating said microorganism in said cell culture medium in a stirred bioreactor at a pH in the range of about 6.8 to 7.2 in an atmosphere containing air, methane and $CO_2$, to increase the amount of said enzyme produced by the microorganism; and
     (d) harvesting the enzyme-enriched microorganism composition provided in step (c).

2. The method of claim 1, wherein the enzyme-enriched microorganism composition is present in the form of a biofilter, and the subsurface groundwater undergoing purification is caused to flow through the biofilter.

3. The method of claim 1, wherein the enzyme-enriched microorganism composition is directly injected into the subsurface groundwater undergoing purification.

4. The method of claim 1, wherein the enzyme is soluble methane monooxygenase.

5. The method of claim 1, wherein the microorganism is a methanotroph.

6. The method of claim 5, wherein the methanotrophic microorganism comprises bacteria of the genus Methylosinus.

7. The method of claim 6, wherein the bacteria are *Methylosinus trichosporium* OB3b.

8. The method of claim 6, wherein the enzyme is soluble methane monooxygenase.

9. The method of claim 5, wherein the methanotrophic microorganism comprises bacteria of the genus Methylococcus.

10. The method of claim 5, wherein the methanotrophic microorganism comprises bacteria of the genus Methylanacas.

11. The method of claim 5, wherein the methanotrophic microorganism comprises bacteria of the genus Methylobacter.

12. The method of claim 5, wherein the methanotrophic microorganism comprises yeast.

13. The method of claim 12, wherein the yeast are Methylotrophic yeast.

14. The method of claim 5, wherein the methanotroph is naturally occurring.

15. The method of claim 5, wherein the methanotroph is recombinantly produced.

16. The method of claim 5, wherein the methanotroph is produced by classical spontaneous or induced mutation and selection methods.

17. The method of claim 1, wherein the microorganism comprises a heterotroph.

18. The method of claim 17, wherein the heterotroph comprises a metal ion reducing bacteria.

19. The method of claim 18, wherein the heterotroph comprises an iron reducing bacteria.

20. The method of claim 17, wherein the heterotroph comprises aerobic heterotrophs.

21. The method of claim 17, wherein the heterotroph comprises fermentative anaerobes.

22. The method of claim 21, wherein the fermentative anaerobes comprises bacteria of the genus Clostridium.

23. The method of claim 17, wherein the heterotroph comprises nitrate reducing bacteria.

24. The method of claim 17, wherein the heterotroph comprises sulfate reducing bacteria.

25. The method of claim 1, wherein the contaminant is an organic material.

26. The method of claim 25, wherein the organic material is selected from the group consisting of volatile halogenated aliphatic compounds, volatile halogenated aromatic compounds, petroleum-related aliphatic compounds, petroleum-related aromatic compounds, and select heterocyclic organics in the pyridine-based groups.

27. The method of claim 1, wherein the contaminant is metallic.

28. The method of claim 1, wherein the contaminant is a radionuclide.

29. The method of claim 1, wherein the microorganism composition is comprised of a mixture of microorganisms and wherein each of the microorganisms is selected so as to target a different enzymatically degradable contaminant.

30. The method of claim 29, wherein the contaminant is comprised of a mixture of contaminants.

31. The method of claim 1, wherein step (c) is carried out at a temperature approximating 30° C.

32. The method of claim 31, wherein step (c) is carried out under an approximately 3:1 v/v 10% $CO_2$-containing air:methane gas mixture.

33. The method of claim 1, wherein step (d) is carried out after about 95 to 120 hours of cell growth.

34. The method of claim 33, wherein step (d) is carried out after the final cell density has reached about 2 to 5 grams of dry cell weight per liter of culture medium.

35. The method of claim 1, wherein the process additionally comprises:

(b1) prior to step (c), further modifying the medium by raising the $NaMoO_4.2H_2O$ approximately 40-fold to concentration of about 16 micromolar and including $NiCl_2$.

36. The method of claim 35, wherein the concentration of $NiCl_2$ in the medium is approximately 7.5 micromolar.

37. The method of claim 35, wherein the process additionally comprises:

(b2) prior to step (c) and after about 80 to 100 hours of cell growth, adding approximately 1× amounts of $FeSO_4.7H_2O$ and $MgSO_4.7H_2O$ to the cell culture medium.

38. The method of claim 37, additionally comprising:

after step (c), further growing the microorganism until the microorganism has reached a resting state.

39. The method of claim 1 wherein said microorganism comprises a methanotroph.

40. The method of claim 39 wherein said methanotroph comprises bacteria of the genus Methylosinus.

41. The method of claim 40 wherein said methanotroph comprises bacteria of the genus *Methylosinus trichosporium* Ob3b.

42. The method of claim 41 wherein the enzyme is soluble methane monooxygenase.

43. A method for purifying subsurface groundwater to remove certain enzymatically degradable contaminants therefrom, comprising the sequential steps of:

(A) providing a microorganism capable of producing an enzyme which allows the intact resting-state cells to degrade the contaminants;

(B) growing the microorganisms under conditions which increase the amount and intracellular longevity of the enzyme, to produce an enzyme-enriched intracellular enzyme longevity-enhanced microorganism composition; and (C) contacting the subsurface groundwater with the enzyme-enriched, intracellular enzyme longevity-enhanced microorganism composition in a resting state;

wherein the microorganism composition having increased whole-cell contaminant-degrading activity is prepared by the process comprising:

(a) providing methanotrophic bacteria of the genus Methylosinus trichosporium Ob3b capable of producing soluble methane monooxygenase;

(b) providing a cell culture medium by modifying Higgin's minimal nitrate salts medium by omitting $CuSO_4.5H_2O$ therefrom, adding approximately 2× $FeSO_4.7H_2O$ and approximately 2× $NaNO_3$ thereto, raising the concentration of $NaMoO_4.2H_2O$ approximately 40-fold to about 16 micromolar, and including $NiCl_2$ at a concentration of approximately 7.5 micromolar;

(c) adding approximately 1× amounts of $FeSO_4.7H_2O$ and $MgSO_4.H_2O$ to the culture medium after about 80 to 100 hours of cell growth;

(d) batch cultivating said microorganism in said cell culture medium in a stirred bioreactor at a pH in the range of about 6.8 to 7.2 at a temperature approximating 30° C. under an approximately 3:1 v/v 10% $CO_2$-containing air:methane mixture, to increase the amount of said enzyme produced by the microorganism;

(e) further growing the microorganisms until the microorganism has reached a resting state; and (f) harvesting the enzyme-enriched microorganism composition provided in step (e), whereby catalytically active, washed resting state cells are provided.

* * * * *